(12) United States Patent
Zhang et al.

(10) Patent No.: US 11,819,514 B2
(45) Date of Patent: Nov. 21, 2023

(54) USE OF OLIGOSACCHARIDE RICLINOCTAOSE IN PREPARATION OF DRUG FOR TREATING AND/OR PREVENTING ISCHEMIA-REPERFUSION INJURY (IRI)

(71) Applicant: Nanjing Southern Element Biotechnology Co., Ltd., Jiangsu (CN)

(72) Inventors: Jianfa Zhang, Jiangsu (CN); Ni Wang, Jiangsu (CN); Yang Zhao, Jiangsu (CN)

(73) Assignee: Nanjing Southern Element Biotechnology Co., Ltd., Nanjing (CN)

( * ) Notice: Subject to any disclaimer, the term of this patent is extended or adjusted under 35 U.S.C. 154(b) by 0 days.

(21) Appl. No.: 17/816,871

(22) Filed: Aug. 2, 2022

(65) Prior Publication Data

US 2023/0054546 A1 Feb. 23, 2023

(30) Foreign Application Priority Data

Aug. 3, 2021 (CN) .......................... 202110887478.0

(51) Int. Cl.
| | |
|---|---|
| *A61K 31/715* | (2006.01) |
| *A61P 9/10* | (2006.01) |
| *A61K 47/02* | (2006.01) |

(52) U.S. Cl.
CPC ............ *A61K 31/715* (2013.01); *A61K 47/02* (2013.01); *A61P 9/10* (2018.01)

(58) Field of Classification Search
None
See application file for complete search history.

(56) References Cited

PUBLICATIONS

Wang, L., Cheng, R., Sun, X., Zhao, Y., Ge, W., Yang, Y., . . . & Zhang, J. (2021). Preparation and gut microbiota modulatory property of the oligosaccharide riclinoctaose. Journal of Agricultural and Food Chemistry, 69(12), 3667-3676. (Year: 2021).*

* cited by examiner

*Primary Examiner* — Dale R Miller
(74) *Attorney, Agent, or Firm* — NKL Law; Allen Xue

(57) ABSTRACT

Oligosaccharide riclinoctaose is used in preparation of a drug for treating and/or preventing ischemia-reperfusion injury (IRI). The oligosaccharide riclinoctaose has a structural formula as follows:

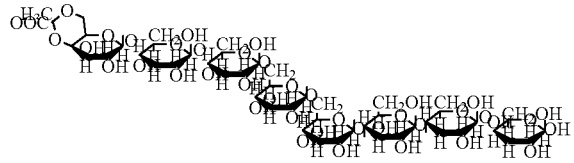

The oligosaccharide riclinoctaose can significantly relieve postoperative liver injury, kidney injury, and brain injury in ischemia-reperfusion mice.

8 Claims, 5 Drawing Sheets

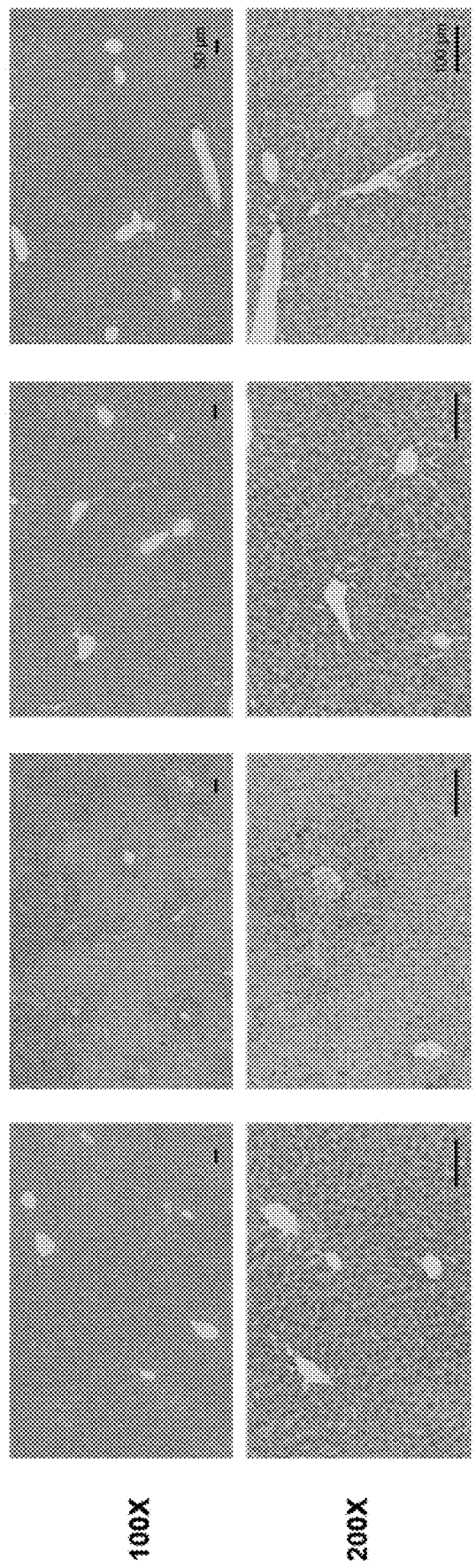

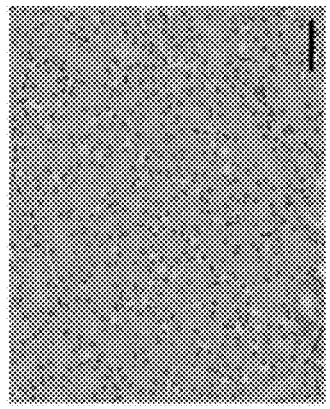
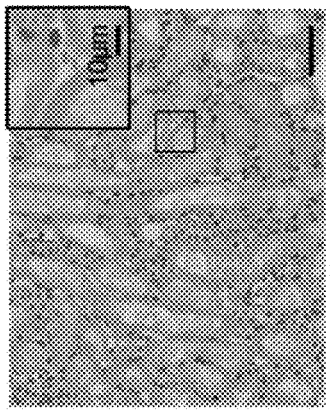
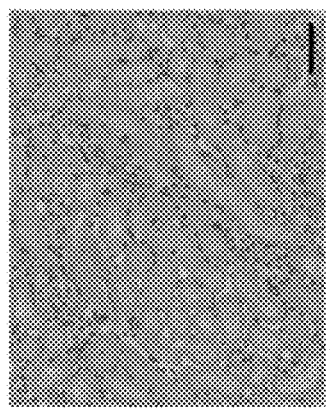
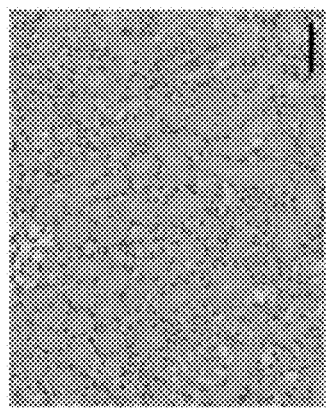
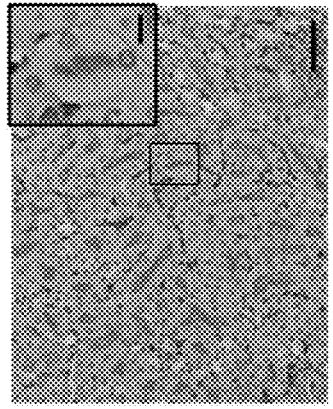
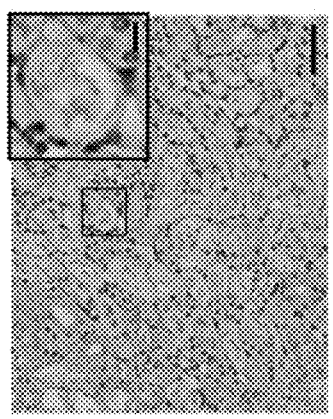
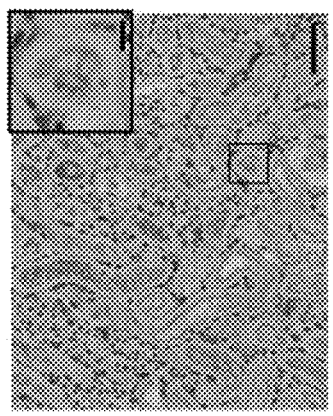
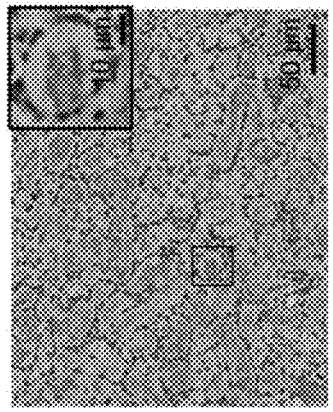
FIG. 4A  FIG. 4B  FIG. 4C  FIG. 4D

USE OF OLIGOSACCHARIDE RICLINOCTAOSE IN PREPARATION OF DRUG FOR TREATING AND/OR PREVENTING ISCHEMIA-REPERFUSION INJURY (IRI)

CROSS REFERENCE TO RELATED APPLICATION

This patent application claims the benefit of priority from Chinese Patent Application No. 202110887478.0, filed on Aug. 3, 2021, the disclosure of which is incorporated by reference herein in its entirety as part of the present application.

TECHNICAL FIELD

The present disclosure belongs to the technical field of drugs for ischemia-reperfusion injury (IRI), and relates to use of oligosaccharide riclinoctaose in preparation of a drug for treating and/or preventing IRI.

BACKGROUND ART

Ischemia-reperfusion injury (IRI) refers to a phenomenon that tissue and organ functions cannot be restored after ischemia and reperfusion, but dysfunction and structural damages are aggravated in the tissues and organs. The pathogenesis of IRI involves multiple mechanisms, including neutrophil activation, oxidative stress, ATP and glycogen depletion, and cellular metabolic stress due to mitochondrial dysfunction. The pathophysiological process has a complex mechanism, and there is currently no comprehensive and effective treatment and specific drugs for the IRI in clinical practice. Liver, kidney, and brain are the common organs affected by IRI in clinical practice. Therefore, it has become an important medical research direction to prevent and treat the IRI.

Oligosaccharide riclinoctaose can be prepared by microbial fermentation and enzymatic hydrolysis. The applicant previously studied and reported oligosaccharide riclinoctaose and a preparation method thereof. The oligosaccharide riclinoctaose has a defined molecular weight, a low viscosity, and a desirable water solubility, and can significantly improve the intestinal microflora as a prebiotic (Wang, L., Cheng, R., Sun, X., et al., Preparation and Gut Microbiota Modulatory Property of the Oligosaccharide Riclinoctaose, J. Agric. Food Chem. 2021 Mar. 31; 69 (12): 3667-3676.). However, it has not yet been reported whether the oligosaccharide riclinoctaose has a protective effect on the IRI.

SUMMARY

The present disclosure provides use of oligosaccharide riclinoctaose in preparation of a drug for treating and/or preventing IRI.

In the present disclosure, the oligosaccharide riclinoctaose has a structural formula as follows:

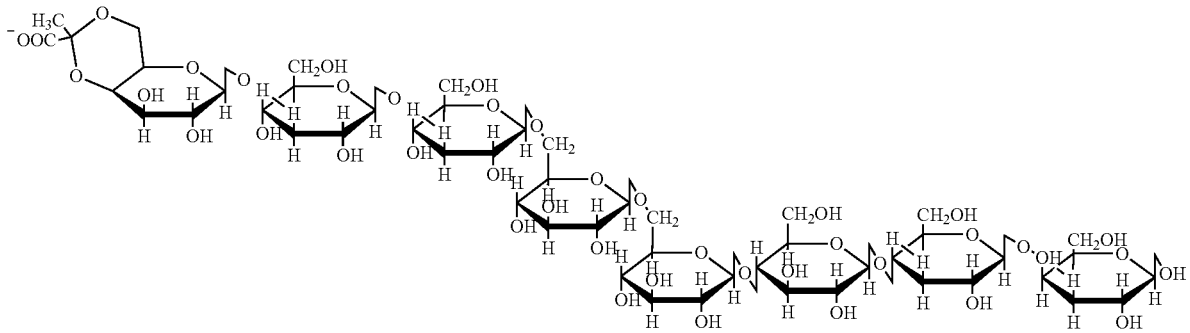

In the present disclosure, the oligosaccharide riclinoctaose includes eight saccharide units, including seven glucose residues and one galactose residue; in the oligosaccharide riclinoctaose molecule, a first glucose residue is ligated to a pyruvate group, and an eighth saccharide unit is a galactose residue.

In the oligosaccharide riclinoctaose, seven glucose residues (Glcp) and one galactose residue (Galp) may be ligated as follows:

D-Glcp(4,6-pyr)-β-(1→3)-D-Glcp-β-(1→3)-D-Glcp-β-(1→6)-D-Glcp-β-(1→6)-D-Glcp-β-(1→4)-D-Glcp-β-(1→4)-D-Glcp-β-(1→3)-D-Galp.

In the present disclosure, the IRI is commonly known in the art, and the IRI may be caused by blood circulation disorder due to factors including but not limited to traumatic shock, surgery, organ transplantation, burn, frostbite, and thrombus.

Specifically, the IRI may include by not limited to hepatic IRI (HIRI), renal IRI (RIRI), cerebral IRI (CIRI), and myocardial IRI (MIRI).

In specific examples of the present disclosure, the enumerated IRI includes the HIRI, the RIRI, and the CIRI.

In the present disclosure, the drug may have a dosage form of an oral preparation, such as a tablet, a capsule, a pill, a powder, a granule, a suspension, and a syrup; the drug may also be in the form of an injection, such as an injection solution and a powder injection through intravenous, intraperitoneal, subcutaneous, or intramuscular routes. All dosage forms are well known to those of ordinary skill in the art of pharmacy.

In the present disclosure, the drug may be administered to any animal that will or has developed the IRI. These animals include human and non-human animals such as pets or livestock.

In the present disclosure, the drug may be administered to a subject by means known in the art, including but not limited to oral, parenteral, subcutaneous, intramuscular, intravenous, intraperitoneal, intrahepatic, intramyocardial, intrarenal, vaginal, rectal, buccal, sublingual, intranasal, and transdermal routes.

In the present disclosure, the drug may have a dosage depending on the age, health and weight of a recipient, as well as a frequency of treatment, and a route of administration and the like.

In specific examples of the present disclosure, the drug has a dosage of 20 mg/mL to 40 mg/mL.

In the present disclosure, a pharmaceutical carrier of the drug may be an injection carrier conventionally used in the art, such as an isotonic NaCl solution, an isotonic glucose solution, or an isotonic solution containing a buffer system, such as a PBS solution.

In specific examples of the present disclosure, the pharmaceutical carrier of the drug is a 0.9% normal saline.

Compared with the prior art, the present disclosure has the following advantages.

(1) The inventors have discovered for the first time that oligosaccharide riclinoctaose can be used as a drug for treatment and/or prevention of IRI; a main mechanism of reducing inflammations is promoting the transition of macrophages from a pro-inflammatory phenotype to an anti-inflammatory phenotype; the oligosaccharide riclinoctaose is safe and non-toxic, has a strong medicinal effect, and has desirable medicinal prospects;

(2) the oligosaccharide riclinoctaose has an effect of alleviating HIRI, can significantly reduce activities of alanine aminotransferase, aspartate aminotransferase, and lactate dehydrogenase, and can reduce a degree of necrotic injury of hepatocytes;

(3) the oligosaccharide riclinoctaose has an effect of alleviating RIRI, can significantly reduce plasma urea nitrogen, creatinine content, and lactate dehydrogenase activity, and can reduce a degree of necrotic injury of nephrocytes;

(4) the oligosaccharide riclinoctaose has an effect of alleviating CIRI, and can significantly improve neurological deficits and reduce cognitive dysfunction; and (5) the drug prepared from the oligosaccharide riclinoctaose has an effect of reducing inflammations caused by the IRI and can significantly ameliorate the pathological state of cells.

BRIEF DESCRIPTION OF THE DRAWINGS

FIG. 1B show an effect of the oligosaccharide riclinoctaose on an aspartate aminotransferase (AST) activity of the mouse liver serum; and FIG. 1C show an effect of the oligosaccharide riclinoctaose on a lactate dehydrogenase (LDH) activity of the mouse liver serum;

FIGS. 2A-2D show an effect of the oligosaccharide riclinoctaose on hepatocyte necrosis, where FIG. 2A show 100× and 200×liver hematoxylin-eosin (H&E) staining images of mice in a sham-operation group (sham); FIG. 2B show 100× and 200×liver H&E staining images of mice in a model group (IR); FIG. 2C show 100× and 200×liver H&E staining images of mice in a low-dosage group (LRO); and FIG. 2D show 100× and 200×liver H&E staining images of mice in a high-dosage group (HRO);

FIG. 3B show an effect of the oligosaccharide riclinoctaose on a creatinine content; and FIG. 3C show an effect of the oligosaccharide riclinoctaose on the LDH activity in mice;

FIGS. 4A-4D show an effect of the oligosaccharide riclinoctaose on nephrocyte and renal tubular necrosis, where FIG. 4A is images of H&E and periodic acid-Schiff (PAS) staining of kidneys of mice in the sham-operation group (sham); FIG. 4B show images of the H&E and PAS staining of kidneys of mice in the model group (IR); FIG. 4C show images of the H&E and PAS staining of kidneys of mice in the low-dosage group (LRO); and FIG. 4D show images of the H&E and PAS staining of kidneys of mice in the high-dosage group (HRO); FIG. 5B show modified neurological severity score (mNSS).

DETAILED DESCRIPTION OF THE EMBODIMENTS

Figure 1A:
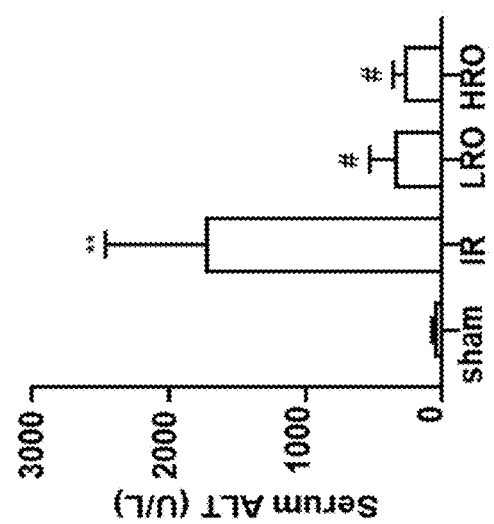
FIGS. 1A-1C show an effect of oligosaccharide riclinoctaose on enzyme activities of mouse liver serum, where FIG. 1A show an effect of the oligosaccharide riclinoctaose on an alanine aminotransferase (ALT) activity of the mouse liver serum.

The present disclosure is described in more detail below with reference to the examples and accompanying drawings.

In the present invention, the oligosaccharide riclinoctaose can be prepared by conventional methods known in the art. Specifically, the oligosaccharide riclinoctaose can be prepared according to a method taught in [Wang, L., Cheng, R., Sun, X. et al., J. Agric. Food Chem., 69, pp. 3667-3676 (2021)].

Unless otherwise specified, all technical and scientific terms used in the present disclosure have the same meaning as commonly understood by one of ordinary skill in the technical field to which the present disclosure belongs.

In order to further define the present disclosure, the following terms and definitions are provided herein.

"Pharmaceutically effective amount" as used herein refers to a dosage required to ameliorate a condition in a mammal.

"IRI" as used herein refers to a phenomenon that tissue and organ functions cannot be restored after ischemia and reperfusion, but aggravate dysfunction and structural damages of the tissues and organs.

"Liver injury" as used herein is pathologically discernible necrosis or apoptosis of hepatocytes.

"Kidney injury" as used herein is pathologically discernible necrosis or apoptosis of nephrocytes.

"Brain injury" as used herein is a behaviorally discernible neurological deficit.

Example 1

Protective Effect of Oligosaccharide Riclinoctaose on HIRI

1. Establishment of Animal Models

The experimental animals were male C57/BL6J mice aged 6 to 8 weeks and weighed 22 g to 26 g. The mice were housed under standard experimental conditions with a 12-hour light-12-hour dark cycle with free access to water and food. The mice were anesthetized with isoflurane, the abdomen was operated on, and the blood supply to middle and left lobes of the liver was blocked with non-invasive hemostatic clips, resulting in 70% hepatic ischemia; after 30 min of ischemia, the clips were removed, and samples were collected to measure biochemical parameters after reperfusion for 6 h.

2. Experimental Grouping

The mice were administered by intraperitoneal injection and randomly divided into four groups; a first group was a sham-operation group (sham), the animals in the sham-operation group received the same laparotomy without vascular clip occlusion; a second group was a model group (IR); a third group was a low-dosage group (LRO), with 20 mg/mL of the oligosaccharide riclinoctaose injected intraperitoneally about 4 h to 6 h before surgery; and a fourth group was a high-dosage group (HRO), with 40 mg/mL of the oligosaccharide riclinoctaose injected intraperitoneally about 4 h to 6 h before surgery. The oligosaccharide riclinoctaose drug was dissolved in a 0.9% normal saline.

3. Serum Enzyme Activity Assay

Whole blood was collected, allowed to coagulate naturally at a room temperature, centrifuged at 2,000 r/min for 10 min, and a supernatant was collected for the determination of ALT, AST and LDH enzyme activities. The activities of AST, ALT and LDH were determined by an enzyme colorimetric quantitative analysis method, according to operation steps in kit instructions, and finally concentrations were determined by colorimetry at a wavelength of 505 nm or 440 nm.

4. Histological Analysis of Liver

The resected liver tissue was immediately fixated with 4% paraformaldehyde (in a PBS buffer), embedded in paraffin, and sections were stained with H&E for histological analysis. The necrosis of hepatocytes was observed by a microscope.

5. Data Analysis

Comparisons between multiple groups were statistically analyzed using a One-way ANOVA statistical method. $P<0.05$ was considered to have a significant effect.

6. Result Analysis

Figure 1B:
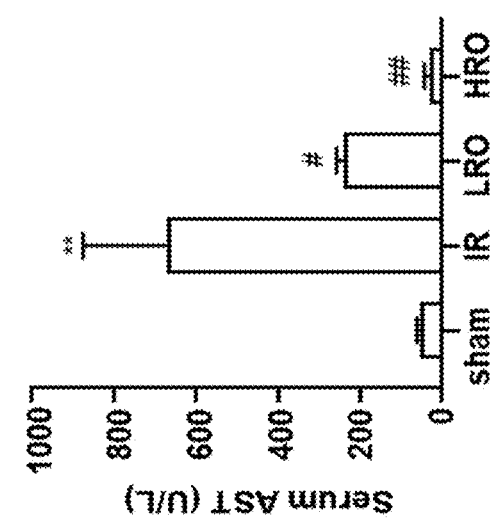
Figure 1C:
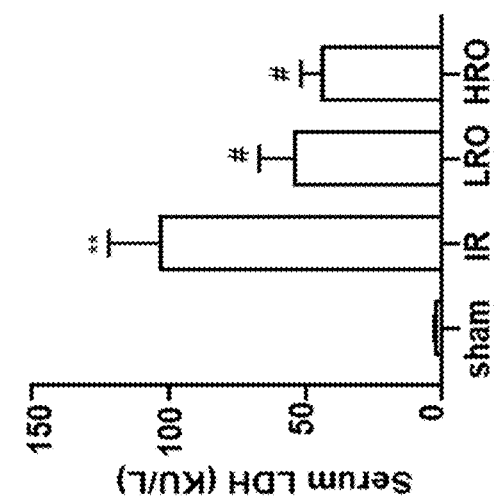

With reference to FIGS. 1A-1C, it can be seen that AST, ALT and LDH may also increase with the aggravation of liver injury; compared with the model group, the AST, ALT and LDH increase in the sham-operation group; while in the treatment groups, the high-dosage group and the low-dosage group are able to decrease the AST, ALT and LDH values in a dosage-dependent manner.

With reference to FIGS. 2A-2D, it can be seen that from the results of H&E staining, the liver tissue structure has changed, and obvious necrosis of liver parenchyma cells and invasion of inflammatory cells can be seen microscopically; the model group has the most irregular tissue morphology, and the most serious tissue damages; the treatment groups and the sham-operation group have the closest tissue morphology, indicating a lesser degree of damages. After treatment of mice with different dosages of the oligosaccharide riclinoctaose, the HIRI can be relieved to different degrees, observing the significant reduction of ALT, AST, LDH activities in serum and the reduction of a necrotic area of liver parenchyma cells.

Example 2

Protective Effect of Oligosaccharide Riclinoctaose on RIRI

1. Establishment of Animal Models

The experimental animals were male C57/BL6J mice aged 6 to 8 weeks and weighed 22 g to 26 g; the mice were anesthetized with isoflurane, and the abdomen was operated on, and after the righting reflex disappeared, the mice were placed in a prone position on a mouse dissection table and fixed; under sterile conditions, the abdominal cavity was opened along a 1.5 cm longitudinal incision on both dorsal sides, the muscles were bluntly separated, and the renal pedicles on both sides were exposed; the blood flow was blocked with a non-invasive vascular clip, and the kidneys turned from red to dark purple, indicating successful ischemia. After 30 min of ischemia, the arterial clips were released, and the abdominal cavity was closed after the kidneys were restored to perfusion; after 24 h, samples were collected to measure biochemical indicators, and an RIRI model was established.

2. Experimental Grouping

The mice were administered by intraperitoneal injection and randomly divided into four groups; a first group was a sham-operation group (sham), the animals in the sham-operation group received the same laparotomy without vascular clip occlusion; a second group was a model group (IR); a third group was a low-dosage group (LRO), with 20 mg/mL of the oligosaccharide riclinoctaose injected intraperitoneally about 4 h to 6 h before surgery; and a fourth group was a high-dosage group (HRO), with 40 mg/mL of the oligosaccharide riclinoctaose injected intraperitoneally about 4 h to 6 h before surgery. The oligosaccharide riclinoctaose drug was dissolved in a 0.9% normal saline.

3. Plasma Biochemical Indicators

Whole blood was collected, allowed to coagulate naturally at a room temperature, centrifuged at 2,000 r/min for 10 min, and a supernatant was collected for the determination of BUN, Creatinine, and LDH. The plasma BUN, Creatinine and LDH concentrations of mice in each group were analyzed according to instructions of the plasma BUN, Creatinine, and LDH detection kits, followed by operation steps in kit instructions, and finally concentrations were determined by colorimetry at a wavelength of 510 nm or 440 nm.

4. Histological Analysis of Kidney

Histomorphological changes in mouse kidneys were analyzed by H&E staining and PAS staining. The resected kidney tissue was immediately fixated with buffered 4% paraformaldehyde (in a PBS buffer) for histological analysis, embedded in paraffin, and sections were stained with by H&E or PAS. The necrosis and structural damages of nephrocytes were observed by a microscope.

5. Data Analysis

Comparisons between multiple groups were statistically analyzed using a One-way ANOVA statistical method. $P<0.05$ was considered to have a significant effect.

6. Result Analysis

Figures 3A, 3B, 3C:
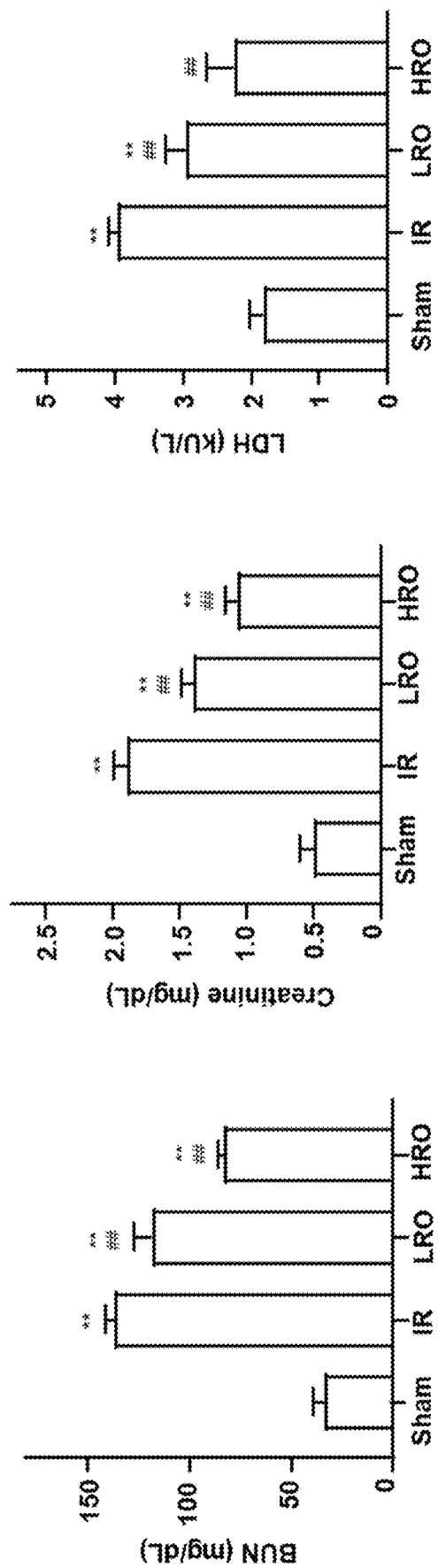
FIGS. 3A-3C show an effect of the oligosaccharide riclinoctaose on urea nitrogen (BUN), creatinine, and LDH in mouse kidney plasma, where FIG. 3A show an effect of the oligosaccharide riclinoctaose on a BUN content.

It can be seen from FIGS. 3A-3C that with the aggravation of renal injury, the BUN and Creatinine are increased significantly, and the LDH is also increased; the BUN and Creatinine are two of the most important indicators of renal function, and acute RIRI can be alleviated in mice after treatment with the oligosaccharide riclinoctaose; the BUN, Creatinine, and LDH each are significantly decreased in the oligosaccharide riclinoctaose treatment group.

As shown in FIGS. 4A-4D, the changes in renal tissue structure can be seen from H&E staining, leading to cell necrosis and invasion of inflammatory factors; for example, the model group has more serious damages, but after treatment with the oligosaccharide riclinoctaose, the area of cell necrosis is reduced, and the infiltration of inflammatory factors is also reduced. It can be seen from the PAS staining that the pathological damage of renal tubules caused by ischemia-reperfusion can be alleviated; in the oligosaccharide riclinoctaose treatment group, the brush border shedding of renal tubule cells and the degree of cell necrosis each are significantly reduced.

Example 3

Protective Effect of Oligosaccharide Riclinoctaose on CIRI

1. Establishment of Animal Models

The experimental animals were male C57/BL6J mice aged 6 to 8 weeks and weighed 22 g to 26 g. Mice were anesthetized with isoflurane and placed on a supine heating pad. The skin was disinfected with iodine and 75% ethanol. A midline neck incision is made to expose the carotid artery (MCA). An external carotid artery (ECA) was isolated and occluded with two knots. An internal carotid artery (ICA) was isolated, and the MCA and ICA were clamped with microvascular clips. A small hole was cut in the ECA between the knot and a bifurcation point. A silicone rubber-coated, 30-mm-long, and 0.11-mm-diameter middle cerebral artery occlusion (MCAO) tether was introduced into the ICA. The artery was opened while sutures were inserted to block the blood vessel. A third knot on the ICA was closed and the suture was secured in a proper place. The mouse abdominal cavity was sutured, and the mice were placed in a heated cage for 30 min, and the wound was closed using small suture clips. The third knot was loosened, the filament was removed, and reperfusion was conducted for 24 h. The skin was closed and the mice were returned to individual cages.

2. Experimental Grouping

The mice were administered by intraperitoneal injection and randomly divided into four groups; a first group was a sham-operation group (sham), the animals in the sham-operation group received the same neck incision without vascular suture blockage; a second group was a model group (IR); a third group was a low-dosage group (LRO), with 20 mg/mL of the oligosaccharide riclinoctaose injected intraperitoneally about 4 h to 6 h before surgery; and a fourth group was a high-dosage group (HRO), with 40 mg/mL of the oligosaccharide riclinoctaose injected intraperitoneally about 4 h to 6 h before surgery. The oligosaccharide riclinoctaose drug was dissolved in a 0.9% normal saline.

3. Detection Indicators

Neurofunctional scoring: the neurobehavioral functions were assessed using mNSS and Longa scores. The mNSS assessed neurological deficits through motor, reflex, sensory, and balance tests. Scores ranged from 0 (indicating no neurological deficit) to 18 (indicating the most severely-injured animal). The Longa score was determined as follows: 0 points, no neurological deficit; 1 point, the animals were unable to fully extend the contralateral forelimbs; 2 points, there was a tail scratching phenomenon when walking (circling to the opposite side); 3 points, a standing posture was unstable, falling to the opposite side; and 4 points, there was no spontaneous walking and loss of consciousness. A score of 0 to 2 was classified as mild nerve injury, while a score of 3 to 4 was classified as severe nerve injury.

4. Data Analysis

Comparisons between multiple groups were statistically analyzed using a One-way ANOVA statistical method. $P<0.05$ was considered to have a significant effect.

5. Analysis of Results

Figure 5B:
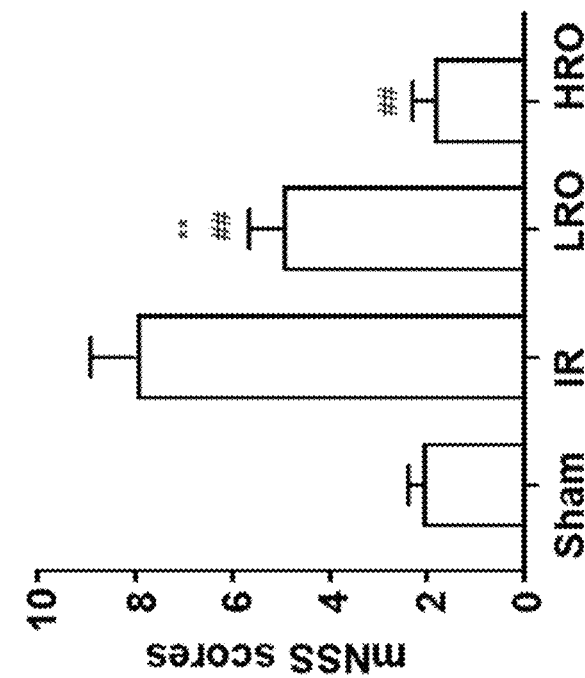
FIGS. 5A and 5B show an effect of the oligosaccharide riclinoctaose on brain-neural functions, where FIG. 5A show Longa score that evaluates neurobehavioral functions.
Figure 5A:
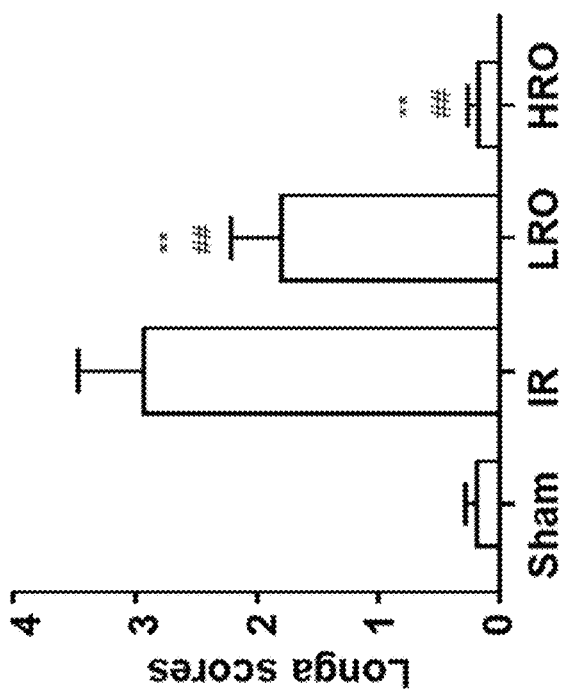

As shown in FIGS. 5A and 5B, it can be seen from the Longa and mNSS scores that the model group (IR) has more serious nerve damages and poor neurological function, and the mice have tail scratching phenomenon (circling to the opposite side) when walking; after treatment by injection of the oligosaccharide riclinoctaose, the neurological deficit of mice can be significantly reduced; for example, although the mice in the low-dosage group (LRO) cannot fully extend the contralateral forelimbs, the mice are not as severe as those in the model group; in contrast, the mice in the high-dosage group (HRO) behave similarly to those in the sham-operation group (sham) without neurological deficits. Therefore, treating mice with different dosages of the oligosaccharide riclinoctaose can alleviate the CIRI to varying degrees.

What is claimed is:

1. A method for treating ischemia-reperfusion injury (IRI) comprising administering to a subject in need thereof a composition comprising an oligosaccharide riclinoctaose, wherein the oligosaccharide riclinoctaose has a structural formula as follows:

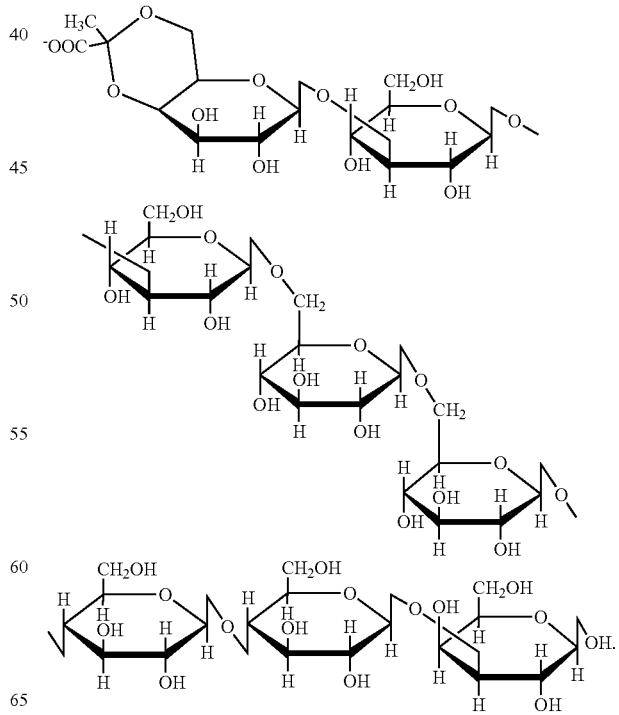

2. The method according to claim 1, wherein in the oligosaccharide riclinoctaose, seven glucose residues and one galactose residue are ligated as follows:

D-Glcp(4,6-pyr)-β-(1→3)-D-Glcp-β-(1→3)-D-Glcp-β-(1→6)-D-Glcp-β-(1→6)-D-Glcp-β-(1→4)-D-Glcp-β-(1→4)-D-Glcp-β-(1→3)-D-Galp.

3. The method according to claim 1, wherein the IRI is caused by blood circulation disorder due to traumatic shock, surgery, organ transplantation, burn, frostbite, or thrombus.

4. The method according to claim 1, wherein the IRI is hepatic IRI (HIRI), renal IRI (RIRI), cerebral IRI (CIRI), or myocardial IRI (MIRI).

5. The method according to claim 1, wherein the composition is administered to a human being or a non-human animal.

6. The method according to claim 1, wherein the composition is administered at a dosage of 20 mg/mL to 40 mg/mL.

7. The method according to claim 1, wherein a pharmaceutical carrier of the composition is an isotonic NaCl solution, an isotonic glucose solution, or an isotonic solution containing a buffer system.

8. The method according to claim 7, wherein the pharmaceutical carrier of the composition is a 0.9% normal saline.

\* \* \* \* \*